United States Patent [19]

Otten et al.

[11] 4,063,927
[45] Dec. 20, 1977

[54] DISULFOXIDE ABSCISSION AGENTS

[75] Inventors: Geneva Gail Otten; Tom Conrad Rheinecker, both of Cincinnati, Ohio

[73] Assignee: The Procter & Gamble Company, Cincinnati, Ohio

[21] Appl. No.: 602,626

[22] Filed: Aug. 7, 1975

[51] Int. Cl.² .............................................. A01N 9/22
[52] U.S. Cl. .......................................... 71/94; 71/74
[58] Field of Search ...................................... 71/94, 74

[56] References Cited
U.S. PATENT DOCUMENTS

| 2,742,476 | 4/1956 | Bernstein et al. | 260/294.8 |
| 3,810,752 | 5/1974 | Merrill | 71/74 X |

Primary Examiner—Lewis Gotts
Assistant Examiner—Catherine L. Mills
Attorney, Agent, or Firm—Ronald L. Hemingway; Douglas C. Mohl; Richard C. Witte

[57] ABSTRACT

A method of inducing fruit abscission by application to a fruit bearing plant of an effective amount of a disulfoxide abscission agent of the formula

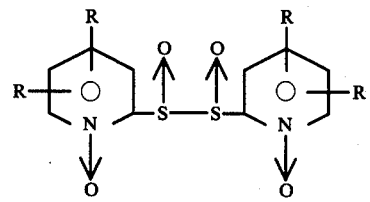

wherein each R is independently selected from the group consisting of hydrogen, hydroxyl, halogen and lower alkyl.

6 Claims, No Drawings

DISULFOXIDE ABSCISSION AGENTS

BACKGROUND OF THE INVENTION

The ability of plants to slough off organs, such as fruit, by an active separation of cells is described by plant physiologists as the process of abscission. Abscission, unaided by mechanical or chemical agents, results from the formation of a starch-filled layer of cells in the area of the fruit rind separating the stem from the fruit. This starch-filled layer is known as the abscission layer. Abscission occurs as the cells in the abscission layer begin to separate, eventually dropping the fruit from the stem. Abscission generally occurs shortly after the fruit has fully matured.

Unfortunately, commercial harvesting of fruit bearing plants very often requires deviation from the natural abscission cycle. Many varieties of fruit bearing plants, such as citrus, reach maturity and are harvested without completion of the abscission cycle. In fact, citrus fruit may actually regreen, i.e., become more tightly attached to the fruit stem, as acceptable maturity standards for eating quality are reached.

When fruit is mechanically harvested without chemical aids and the cells of the abscission layer have not begun to separate or the fruit has begun to regreen, a great deal of force is required to remove the fruit. Often when adequate force to remove the fruit is applied to the fruit or fruit bearing plant, a break or tear may take place and a plug of tissue may be removed from the fruit rind; sometimes the fruit stem is broken, leaving a jagged woody stem attached to the fruit; or the fruit bearing plant itself is injured.

It is apparent that a means of facilitating abscission would not only minimize fruit damage, but also maximize harvest productivity. The quality of the fruit would increase because of less damage, and the yield per tree would increase because of more uniform and complete harvest.

A wide variety of chemicals have been used to regulate the abscission process of fruit bearing plants in attempts to facilitate harvesting. Such chemicals are called, in general terms, harvesting aids or abscission agents. Typical abscission agents are designed and formulated to loosen fruit at the time of harvest. For example, U.S. Pat. No. 3,810,752, granted May 14, 1974, describes the use of pyridine-N-oxides to loosen harvested fruit without significant damage to the rest of the plant. However, previously known abscission agents suffer shortcomings. For example, some agents abscise not only mature fruit, but immature fruit as well, thereby reducing the succeeding year's crop. Many agents abscise leaves as well as fruit also reducing the succeeding year's crop. Finally, many agents cause pre-harvest drop which results in considerable crop loss due to ground-rotting.

Thus, a suitable abscission agent is one which facilitates fruit harvesting without causing abscission of the immature fruit or leaves, or premature ripening. Copending application Ser. No. 602,610, Bednarz and Otten, filed Aug. 7, 1975, now abandoned discloses the use of bis(2-pyridine-N-oxide)disulfides as fruit abscission agents. Copending application Ser. No. 602,335, Otten and Rheinecker, filed Aug. 6, 1975, now abandoned discloses the use of bis(2-pyridine-N-oxide)disfulfones as fruit abscission agents.

SUMMARY OF THE INVENTION

The present invention provides an improved method for inducing fruit abscission by application to a fruit bearing plant of an effective amount, generally within the range of from about 5 pounds per acre to 100 pounds per acre, of a disulfoxide abscission agent of the formula

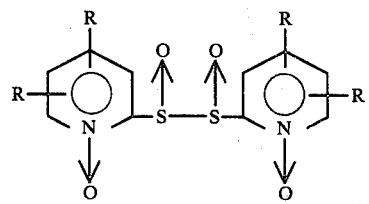

wherein each R is independently selected from the group consisting of hydrogen, hydroxyl, halogen and lower alkyl.

In its composition aspects the present invention provides concentrates of the above abscission agents additionally comprising a non-phytotoxic surfactant.

DETAILED DESCRIPTION OF THE INVENTION

The present invention relates to the discovery that disulfoxide compounds of the formula

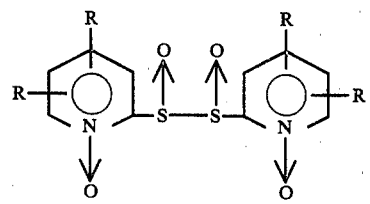

wherein each R is independently selected from the group consisting of hydrogen, hydroxyl, halogen, and lower alkyl containing from 1 to about 10 carbon atoms can be applied to a fruit bearing plant to induce fruit abscission.

The disulfoxides useful as abscission agents in the present invention are well known and are prepared in accordance with conventional procedures. In general, the disulfoxides useful herein can be prepared by the oxidation of selected omadine disulfides with hydrogen peroxide in ethanol at room temperature.

Disulfoxides suitable for use in the present invention include those compounds, according to the above formula, wherein either pyridine ring may be monosubstituted, disubstituted, or unsubstituted. Suitable ring substituents, represented by "R" in the above formula, include hydroxyl; lower alkyl, such as methyl, ethyl, propyl, isobutyl, hexyl, octyl, or decyl; and halogen, such as chloro, bromo, or iodo.

Preferred compounds include, for example, the substituted or unsubstituted bis(2-pyridine-N-oxide) disulfoxides wherein both pyridine rings are identically substituted or unsubstituted. Specific bis(2-pyridine-N-oxide)disulfoxides suitable for use in the present invention include, for example, bis[2-(3-hydroxy)pyridine-N-oxide]disulfoxide; bis[2-(3,4-dihydroxy)pyridine-N-oxide]disulfoxide; bis[2-(5-methyl)pyridine-N-oxide]disulfoxide; bis[2-(6-ethyl)pyridine-N-oxide]disulfoxide; bis[2-(4,6-dipropyl)pyridine-N-oxide]disulfoxide; bis[2-(4-methyl-5-ethyl)pyridine-N-oxide]disulfoxide; bis[2-(3-decyl) pyridine-N-oxide]disulfoxide; bis[2-(3,4- dibutyl)pyridine-N-oxide]disulfoxide; bis[2-(3-hydroxy-4-hexyl)pyridine-N-oxide]disulfoxide; bis[2-(5-hydroxy-6-heptyl)pyridine-N-oxide]disulfoxide; bis[2-(3-chloro)-pyridine-N-oxide]disulfoxide; bis[2-(4-bromo)pyridine-N-oxide]disulfoxide; bis[2-(3,4-dichloro)pyridine-N-oxide]disulfoxide; bis[2-(5-bromo-6-chloro)pyridine-N-oxide]disulfoxide; bis[2-(3-hydroxy-4-chloro)pyridine-N-oxide]disulfoxide; and bis[2-(3-hexyl-5-bromo)pyridine-N-oxide]disulfoxide.

Bis[2-pyridine-N-oxide]disulfoxide is the most preferred compound of the present invention.

In use, the present invention encompasses applying a safe and effective amount of a disulfoxide compound, as defined above, to a fruit bearing plant to induce fruit abscission. The term "fruit bearing plant" is intended to include the major types of fruit, for example, berries such as grapes, tomatoes, blueberries, and oranges; drupes such as peaches, cherries, olives, plums and walnuts; aggregate fruits such as blackberries and raspberries; multiple fruits such as pineapples, figs and mulberries; and accessory fruits such as apples, pears and strawberries. A thorough description of various other fruit bearing plants which may be treated in accordance with the present invention can be found in *General Botany*, Fuller and Richie, Barnes and Noble Inc. 1969, incorporated herein by reference.

The abscission agents of the present invention may be used alone or as mixtures. It must be understood, however, that in use the disulfoxides are preferably incorporated into compositions comprising the abscission agent and a non-phytotoxic plant-compatible surfactant. As used herein, a plant-compatible surfactant is defined as a surfactant which has substantially no phytotoxic properties and provides a means whereby the disulfoxide compounds can be diluted prior to application. Accordingly, this invention provides concentrate compositions which enable the compounds herein to be practically and conveniently diluted and applied to fruit bearing plants at proper use levels.

Surfactants suitable for use in the foregoing solid and liquid compositions can be anionic, cationic, nonionic, amphoteric, and zwitterionic types.

Examples of suitable anionic surface active agents for use herein are sodium salts of fatty alcohol sulfates having from 8–18 carbon atoms in the fatty chain and sodium salts of alkyl benzene sulfonates having from 9 to 15 carbon atoms in the alkyl chain. Examples of suitable nonionic surface active agents are the polyoxyethylene adducts of fatty alcohols having 10 to 18 carbon atoms and the polyethylene oxide condensates of alkyl phenols, wherein the alkyl chain contains from about 6 to 12 carbon atoms and the amount of ethylene oxide condensed onto each mole of alkyl phenol is from about 5 to 25 moles. Preferred herein are the polyethylene oxide condensates of sorbitan monooleate (Tweens) wherein the amount of ethylene oxide condensed onto each mole of sorbitan monooleate is about 10 to 40 moles. Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing group, e.g., sulfate or sulfonate. Specific suitable ampholytic surface active agents are sodium-3-dodecylaminoproprionate and sodium-3-dodecyl amino propane sulfonate. Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio)propane-1-sulfonate and 3-(N,N-dimethyl-N-hexadecylammonio)-2-hydroxy propane-1-sulfonate. Many other suitable surface active agents are described in "Detergents and Emulsifiers — 1973 Annual", John W. McCutcheon, Inc. When used in the liquid compositions herein for direct application to plants, the surface active agents should be present at levels from about 0.001% to about 10.0% and preferably from about 1.0% to about 5.0% by weight of the compositions.

The concentrates of this invention which are emulsifiable and/or soluble comprise from about 10% to about 80%, preferably from about 20% to about 60%, by weight, of a disulfoxide compound selected from the group consisting of compounds of the formula

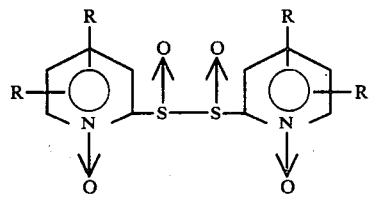

wherein each R is independently selected from the group consisting of hydrogen, hydroxyl, halogen and lower alkyl; and from about 1% to 20%, preferably from about 1% to 10%, by weight, of a non-phytotoxic, plant-compatible surface active agent. Of course, such concentrates may optionally contain other biologically active adjuvants or fillers, as detailed hereinafter.

To what extent such compositions should be diluted prior to use will depend upon the formulation of the composition, the method of application and the proper usage level for the plant being treated. For example, aqueous compositions will generally be in the form of concentrates which will require dilution to proper use levels. Generally, it would not be economically feasible to supply compositions containing less than 30%, by weight, of the active disulfoxide compound. Although it is difficult to specify exact dilution levels for all applications, it has been found that dilution to from about 2,000 parts per million of disulfoxide active (ppm) to about 8,000 ppm is suitable for most purposes.

As previously noted, compositions of the present invention can be solids, such as dusts or wettable powders, or they can be liquids such as solutions, emulsions, or aerosols.

Abscission inducing compositions in the form of dusts may be prepared by grinding and blending the disulfoxide compounds described above with a solid carrier such as talc, clay, silica, pyrophylite or solid fertilizers. Granular compositions can be prepared by impregnating the disulfoxide, usually dispersed or dissolved in the suitable solvent, onto or into granulated carriers such as the attapulgites or vermiculites, or granulated solid fertilizers. Usually a particle range of from 0.01 mm. to 1.5 mm. is preferred. Wettable powders, which can be dispersed in water or oil to any desired concentration, can be prepared by incorporating surface active agents, as described below, into the concentrated dust compositions.

A preferred embodiment herein encompasses the disulfoxide compounds in plant-substantive formulations. The term "plant-substantive" is intended to encompass formulations which mechanically or chemically adhere to the tree thereby resisting removal. Preferred materials suggested as plant-substantive agents include various waxes and paraffins, polymers, and sulfur. Wax coated compositions can be formulated by dispersing the active ingredients in molten wax, forming the dispersion into small particles, and cooling the composition below the melting point of the wax. The water resistance of the particles can be controlled by increasing or decreasing the amount of wax employed so as to provide proper release for climatic conditions encountered. In areas of relatively heavy rainfall, the water resistance should normally be high in the amount of wax and the dispersion should be relatively high also. Conversely, in relatively dry areas the amount of wax should be relatively low. In addition, various additives can be dissolved in the wax phase in order to improve the water resistance of the composition or effect other benefits. U.S. Pat. No. 3,252,786, incorporated herein by reference, discloses the use of rosins or asphalts as effective slow-release additives. Other additives can be used, for example, to provide anti-caking properties. Elemental sulfur is an essential plant nutrient in many areas. Thus, its use as a coating agent provides additional nutritive benefits. Sulfur coatings, however, tend to be very porous and present serious leaching problems. Therefore, sulfur-coated compositions usually contain a sealant material. Various sealants suitable for use herein include, for example, petrolatum, waxes and boiled linseed oil. Additives are useful to increase sulfur continuity and render the coating less permeable to moisture.

Fruit abscising compositions in liquid form can be prepared by dissolving from about 30%, by weight, to saturation of the disulfoxide compounds and a non-phytotoxic surfactant in liquid carriers. Water and water containing from about 0.1% to about 10%, preferably 1%, by weight, of 1,2-propylene glycol are preferred aqueous carriers. Such aqueous solutions can be dispersed on fruit bearing plants under superatmospheric pressures as aerosols. In addition to 1,2-propylene glycol, other glycols and lower alcohols, such as 1,3-propylene glycol, liquid vicinal polyols having a molecular weight below about 3,000, ethanol, propanol, butanol, and the like, are suitable in such compositions.

It will be well understood by any plant biologist that, as with any plant regulation agent, the abscission inducing compositions containing the disulfoxides and a plant-compatible surfactant should be applied to particular fruit bearing plants at certain optimum application rates (i.e., weight of agent for unit of cultivated ground area) and at certain stages in the fruit bearing cycle of the plant if they are to achieve optimal abscission regulant effects. The abundant variety of fruit bearing species coupled with the wide range of climatic and soil conditions which may be encountered make it difficult to specify exact application rates for all purposes. For general guidance, when applied broadcast to fruit bearing plants, the term "safe and effective amount" based on weight of disulfoxide compound will include application at a rate of at least about 5 pounds per acre. Normally a range of from about 5 pounds per acre to about 100 pounds per acre and preferably within the range of from about 10 pounds to about 20 pounds per acre per application is suitable. For some purposes repeated applications may be desirable.

Another aspect of the present invention encompasses solid and liquid abscising compositions which include, in addition to the disulfoxide and surfactant, a safe and effective amount of other biologically active adjuvants. As used herein the term "biologically active adjuvant" includes insecticides, fungicides, herbicides, fertilizers, antimicrobial agents, and the like. The selection of adjuvants depends primarily upon the needs of the individual user. Such adjuvants are compatible with the intended uses of the disulfoxides and the beneficial properties of such adjuvants control related problems such as weed and insect infestation, plant diseases and microbial degradation of the active. The preferred adjuvants for use herein are herbicides, insecticides, anti-microbial agents and fertilizers.

The following examples are illustrative of the present invention.

EXAMPLE I

Five hundred milliliters of an aqueous spray formulation are prepared by diluting 2 grams of bis(2-pyridine-N-oxide)disulfoxide and 5 grams of Surfactant X-77* with water. This formulation corresponds to a concentration of 4000 parts per million of disulfoxide active.

*A proprietary surfactant mixture comprising alkylaryl polyoxyethylene glycols, free fatty acids, and isopropanol available from Colloidal Products Corporation.

The bis(2-pyridine-N-oxide)disulfoxide formulation is applied to the branch of a Hamlin orange. Seven days after treatment 10 fruit are removed from the treated branch with the stems still attached and the force required to separate the fruit from the attached stem is recorded. Similarly, 10 untreated fruit are removed with their stems still attached and the force required to separate the fruit from the stems of the untreated group is recorded. It is found that the treated fruit are too loose to pull, i.e., the force required to remove the fruit is too small to measure, while the control fruit require a significant force to pull the fruit from the stem.

EXAMPLE II

Five hundred milliliters of an aqueous bis(2-pyridine-N-oxide)disulfoxide spray formulation are prepared by diluting 2 grams of bis(2-pyridine-N-oxide)disulfoxide and 5 grams of Surfactant X-77 with water. This formulation corresponds to a concentration of 4,000 parts per million of disulfoxide active.

The diluted formulation is applied to the branch of a Valencia orange. Seven days after treatment 10 fruit were removed from the treated branch with the stems still attached and the force required to separate the fruit from the attached stems is measured. Similarly, 10 untreated fruit are removed with the stems still attached and the force required to separate the untreated fruit from their stems is recorded. The treated fruit are too loose to pull, while the control group require a significant force to pull the fruit from the stem.

EXAMPLE III

Three 500 milliliter aqueous spray formulations are prepared by combining 1, 2, and 4 gram aliquots of bis(2-pyridine-N-oxide)disulfoxide with 5 grams of Surfactant X-77. These formulations correspond to concentrations of 2,000, 4,000 and 8,000 parts per million of disulfoxide active, respectively.

Each of the bis(2-pyridine-N-oxide)disulfoxide formulations is applied to the branch of a Valencia orange. Seven days after treatment 10 fruit are removed from each of the treated branches with the stems still attached and the force required to separate the fruit from the attached stem is recorded. Similarly, 10 untreated fruit are removed with their stems still attached and the force required to separate the fruit from the stems of the untreated group is recorded. It is found that on the branches treated with the formulations having 4,000 and 8,000 ppm of disulfoxide the fruit are too loose to pull, i.e., the force required to remove the fruit is too small to measure. The fruit treated with the formulation corresponding to 2,000 ppm requires considerable force to remove it but less than the force required to remove the fruit from the control.

EXAMPLE IV

Five hundred milliliters of an aqueous 2,000 ppm bis(2-pyridine-N-oxide)disulfoxide spray formulation are prepared by combining 1 gram of bis(2-pyridine-N-oxide) disulfoxide with 5 grams of Surfactant X-77.

The diluted formulation is applied to the branch of a Valencia orange very late in the picking season. Seven days after treatment 10 fruit are removed from the treated branch with the stems still attached and the force required to separate the fruit from the attached stems is measured. Similarly, 10 untreated fruit are removed with the stems still attached and the force required to separate the untreated fruit from their stems is recorded. The treated fruit are too loose to pull, while the control group require a significant force to pull the fruit from the stem.

EXAMPLE V

Five gallons of an aqueous spray formulation are prepared by combining 75.7 grams of bis(2-pyridine-N-oxide)disulfoxide with 189.25 grams of Surfactant X-77.

The bis(2-pyridine-N-oxide)disulfoxide formulation is applied to two mature Valencia orange trees. Seven days after treatment fruit are removed from the treated trees and the force required to separate the fruit from their stems is observed. Similarly, fruit are removed from an untreated Valencia orange tree and the force required to separate the fruit from their stems is recorded. It is found that the vast majority of treated fruit are too loose to pull, i.e., the force required to remove the fruit is too small to measure, while the control fruit require a significant force to pull the fruit from the stem.

The following disulfoxides are substituted for bis(2-pyridine-N-oxide)disulfoxide in the above aqueous formulation and effective fruit abscission agents are provided: bis[2-(3-hydroxy)pyridine-N-oxide]disulfoxide; bis[2-(3,4-dihydroxy)pyridine-N-oxide]disulfoxide; bis[2-(5-methyl)pyridine-N-oxide]disulfoxide; bis[2-(6-ethyl)pyridine-N-oxide]disulfoxide; bis[2-(4,6-dipropyl)pyridine-N-oxide]disulfoxide; bis[2-(4-methyl-5-ethyl)pyridine-N-oxide]disulfoxide; bis[2-(3-decyl)pyridine-N-oxide]disulfoxide; bis[2-(3,4-dibutyl)pyridine-N-oxide]disulfoxide; bis[2-(3-hydroxy-4-hexyl)pyridine-N-oxide]disulfoxide; bis[2-(5-hydroxy-6-heptyl)pyridine-N-oxide]disulfoxide; bis[2-(3-chloro)pyridine-N-oxide]disulfoxide; bis[2-(4-bromo)pyridine-N-oxide]disulfoxide; bis[2-(3,4-dichloro)pyridine-N-oxide]disulfoxide; bis[2-(5-bromo-6-chloro)pyridine-N-oxide]disulfoxide; bis[2-(3-hydroxy-4-chloro)pyridine-N-oxide]disulfoxide; and bis[2-(3-hexyl-5-bromo)pyridine-N-oxide]disulfoxide.

What is claimed is:

1. A method of inducing fruit abscission by application to a fruit bearing plant of an effective amount of a disulfoxide abscission agent of the formula

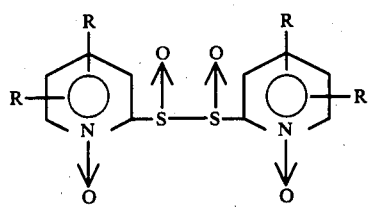

wherein each R is independently selected from the group consisting of hydrogen, hydroxyl, halogen and lower alkyl containing from 1 to about 10 carbon atoms.

2. A method according to claim 1 wherein said disulfoxide compound is bis(2-pyridine-N-oxide)disulfoxide.

3. A method of inducing fruit abscission by application to a fruit bearing plant of an effective amount of a disulfoxide abscission agent of the formula

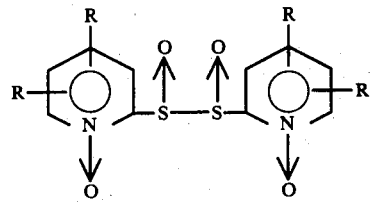

wherein each R is independently selected from the group consisting of hydrogen, hydroxyl, halogen and lower alkyl containing from 1 to about 10 carbon atoms; and a non-phytotoxic plant-compatible surface active agent.

4. A method according to claim 3 wherein said disulfoxide compound is bis(2-pyridine-N-oxide)disulfoxide.

5. The method of claim 3, wherein the fruit is citrus.

6. The method of claim 4, wherein the fruit is citrus.

* * * * *